United States Patent [19]

Friebe et al.

[11] Patent Number: 4,904,666

[45] Date of Patent: Feb. 27, 1990

[54] PYRAZOLO(3,4-D)PYRIMIDINE COMPOUNDS, COMPOSITIONS AND METHOD OF USE

[75] Inventors: Walter-Gunar Friebe, Mannheim; Wolfgang Kampe, Heddesheim; Otto-Henning Wilhelms, Weinheim-Rittenweier, all of Fed. Rep. of Germany

[73] Assignee: Boehringer Mannheim GmbH, Mannheim, Fed. Rep. of Germany

[21] Appl. No.: 181,729

[22] Filed: Apr. 14, 1988

[30] Foreign Application Priority Data

Apr. 15, 1987 [DE] Fed. Rep. of Germany ....... 3712735

[51] Int. Cl.$^4$ .................. C07D 487/04; A61K 31/505
[52] U.S. Cl. ..................................... 514/258; 544/262
[58] Field of Search ......................... 544/262; 514/258

[56] References Cited

U.S. PATENT DOCUMENTS 3,682,918  8/1972  Druey et al. ........................ 544/262
3,720,674  3/1973  Breuer et al. ....................... 544/262

Primary Examiner—Mukund J. Shah
Assistant Examiner—C. L. Cseh
Attorney, Agent, or Firm—Felfe & Lynch

[57] ABSTRACT

The present invention provides pyrazolo[3,4-d]-pyrimidines of the general formula:

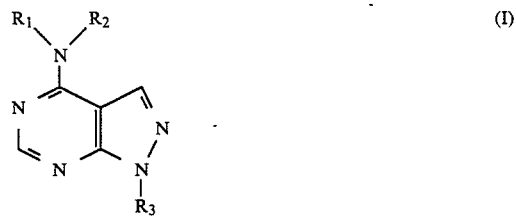

wherein $R_1$ is a $C_1$ to $C_6$-alkyl radical, a $C_2$ to $C_6$-alkenyl radical, a $C_3$ to $C_7$-cycloalkyl radical or an aryl radical, $R_2$ is a $C_2$ to $C_6$-alkenyl radical, a $C_3$ to $C_7$-cycloalkyl radical or an aralkyl or hetaralkyl radical with 1 to 6 carbon atoms in the alkyl moiety and substituted, if desired, one or more times by halogen, $C_1$ to $C_6$-alkyl, hydroxyl, $C_1$ to $C_6$-alkoxy, $C_1$ to $C_3$-haloalkyl, $C_3$ to $C_7$-alkoxy carbonyl, aminocarbonyl, $C_2$ to $C_7$-alkylaminocarbonyl, $C_3$ to $C_{13}$-dialkylaminocarbonyl, cyano or $C_1$ to $C_6$-alkylthio and $R_3$ is a hydrogen atom or a $C_2$ to $C_6$-alkyl radical substituted, if desired, one or more times by hydroxyl or is a tetrahydrofuranyl or tetrahydropyranyl radical, with the proviso that $R_2$ cannot be an unsubstituted benzyl radical when $R_1$ is a methyl radical, and the physiologically acceptable salts thereof with inorganic and organic acids.

The present invention also provides processes for the preparation of these compounds and pharmaceutical compositions containing them.

21 Claims, No Drawings

PYRAZOLO(3,4-D)PYRIMIDINE COMPOUNDS, COMPOSITIONS AND METHOD OF USE

The present invention is concerned with new pyrazolo[3,4-d]pyrimidines, processes for the preparation thereof and pharmaceutical compositions containing them.

The new pyrazolo[3,4-d]pyrimidines according to the present invention are compounds of the general formula:

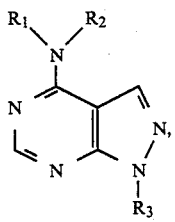

wherein $R_1$ is a $C_1$ to $C_6$-alkyl radical, a $C_2$ to $C_6$-alkenyl radical, a $C_3$ to $C_7$-cycloalkyl radical or an aryl radical, $R_2$ is a $C_2$ to $C_6$-alkenyl radical, a $C_3$ to $C_7$-cycloalkyl radical or an aralkyl or hetaralkyl radical with 1 to 6 carbon atoms in the alkyl moiety and substituted, if desired, one or more times by halogen, $C_1$ to $C_6$-alkyl, hydroxyl, $C_1$ to $C_6$-alkoxy, $C_1$ to $C_3$-haloalkyl, $C_3$ to $C_7$-alkoxycarbonyl, aminocarbonyl, $C_2$ to $C_7$-alkylaminocarbonyl, $C_3$ to $C_{13}$-dialkylaminocarbonyl, cyano or $C_1$ to $C_6$-alkylthio and $R_3$ is a hydrogen atom or a $C_2$ to $C_6$-alkyl radical substituted, if desired, one or more times by hydroxyl or is a tetrahydrofuranyl or tetrahydropyranyl radical, with the proviso that $R_2$ cannot be an unsubstituted benzyl radical when $R_1$ is a methyl radical and the physiologically acceptable salts thereof with inorganic and organic acids.

4-[N-(Benzyl)-methylamino]-1H-pyrazolo[3,4-d]pyrimidine is known from J. Med. Chem., 5, 588/1962 as a potential antitumour agent.

When compounds of general formula I contain an asymmetric carbon atom, the optically-active compounds and racemic mixtures are also the subject of the present invention.

The new compounds of general formula I display valuable pharmacological properties; in particular, they can inhibit the antigen-caused liberation of mediators from lung tissue samples, as well as the contraction of lung tissue strips. Therefore, they can be used for the treatment of allergic diseases, as well as of inflammation-caused bronchospastic and bronchoconstrictory reactions.

The alkyl moieties in the said radicals, as well as the alkenyl, alkoxy, alkylamino and alkylthio radicals, can be straight-chained or branched. Preferred alkyl radicals include methyl, ethyl, n-propyl, isopropyl, n-butyl, isobutyl, n-pentyl and 3-pentyl radicals. An alkenyl radical is preferably the allyl radical. Preferred alkoxy and alkylthio radicals include the methoxy, ethoxy, methylthio and ethylthio radicals.

Cycloalkyl radicals are preferably cyclopentyl and cyclohexyl radicals.

Heteroalkyl radicals are preferably the furfuryl, thenyl and pyridinylmethyl radicals.

Preferred aralkyl radicals include, for example, the benzyl, phenethyl, phenylpropyl, phenylisopropyl and 3-methyl-3-phenylpropyl radicals.

Heteroalkyl radicals contain, for example, five- or six-membered rings with one or two nitrogen, oxygen or sulphur atoms; in the case of two hetero atoms, these can be the same or different.

As a rule, an aryl radical is a naphthyl or phenyl radical and preferably a phenyl radical.

Halogen atoms are especially fluorine, chlorine, bromine and iodine.

$R_3$ is preferably a hydrogen atom or a 2-hydroxyethyl, 2-hydroxypropyl, 2,3-dihydroxypropyl, tetrahydrofuran-2-yl or tetrahydropyran-2-yl radical.

Apart from the compounds mentioned in the Examples, the present invention also includes, in particular, all compounds which display every possible combination of the substituents mentioned in the Examples.

The compounds according to the present invention can be prepared, for example, by reacting in known manner a compound of the general formula:

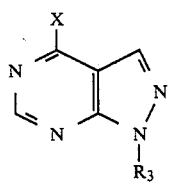

wherein X is a reactive residue and $R_3$ has the above-mentioned meaning, with a compound of the general formula:

$$HNR_1R_2 \qquad (III),$$

wherein $R_1$ and $R_2$ have the above-mentioned meanings, and subsequently, if desired, a radical $R_3$ is replaced by another radical given by the definition of $R_3$ and a compound obtained of general formula I is converted, if desired, by neutralisation with a non-toxic acid into a pharmacologically acceptable salt thereof.

The reactive residue X can be, for example, a chlorine or bromine atom or a lower alkylthio radical.

Conversion of a compound of general formula I in which $R_3$ is a hydrogen atom into a compound of general formula I in which $R_3$ is other than a hydrogen atom preferably takes place by alkylation with a compound of the general formula $R_3$-Y, wherein Y is a reactive residue, for example a halogen atom or a methanesulphonyloxy or toluenesulphonyloxy radical, in an acid binding medium. Hydroxyl substituents possibly present in $R_3$ can be protected by ether, ester or ketal groups and liberated after the alkylation.

For the removal of a tetrahydrofuranyl or tetrahydropyranyl radical $R_3$, there can be used an inorganic acid, such as hydrochloric acid or sulphuric acid, in aqueous or organic solution.

On the other hand, by proton catalysis, into compounds of general formula I, in which $R_3$ is a hydrogen atom, there can be introduced a tetrahydrofuranyl or tetrahydropyranyl radical by reaction with excess 2,3-dihydrofuran or 2,3-dihydropyran.

The starting compounds of general formulae II and III are either known from the literature or can be prepared analogously to processes known from the literature.

The pharmacologically acceptable salts are obtained in the usual way, for example by neutralisation of compounds of general formula I with non-toxic inorganic or organic acids, for example hydrochloric acid, sulphuric acid, phosphoric acid, hydrobromic acid, acetic acid, lactic acid, citric acid, malic acid, salicylic acid, malonic acid, maleic acid or succinic acid.

For the preparation of pharmaceutical compositions, compounds of general formula I are mixed in known manner with appropriate pharmaceutical carrier substances, aroma, flavouring and colouring materials and formed, for example, into tablets or dragees or, with the addition of appropriate adjuvants, suspended or dissolved in water or an oil, for example olive oil.

The compounds of general formula I can be administered orally and parenterally in liquid or solid form. As injection medium, water is preferably used which contains stabilising agents, solubilising agents and/or buffers usual in the case of injection solutions. Such additives include, for example, tartrate and borate buffers, ethanol, dimethyl sulphoxide, complex formers (such as ethylenediamine-tetraacetic acid), high molecular weight polymers (such as liquid polyethylene oxide) for viscosity regulation and polyethylene derivatives of sorbite anhydrides. Solid carrier materials include, for example, starch, lactose, mannitol, methyl cellulose, talc, highly dispersed silicic acids and high molecular weight polymers (such as polyethylene glycols).

Compositions suitable for oral administration can, if desired, contain flavouring and sweetening agents.

For external use, the compounds I according to the present invention can also be used in the form of powders and salves. For this purpose, they are mixed, for example, with powdered, physiologically acceptable dilution agents or conventional salve bases.

The dosage administered depends upon the age, the state of health and the weight of the recipient, the extent of the disease, the nature of further treatments possibly carried out simultaneously, the frequency of the treatments and the nature of the desired action. Usually, the daily dose of the active compounds is from 0.1 to 50 mg./kg. body weight. Normally, 0.5 to 40 and preferably 1.0 to 20 mg./kg. per day, in one or more administrations per day, are effective in order to obtain the desired results.

Especially preferred according to the present invention are, apart from the compounds mentioned in the Examples, also the following:

4-{N-[1-(3-bromophenyl)-ethyl]-cyclopentylamino}-1H-pyrazolo[3,4-d]pyrimidine
4-{N-[2-(3-bromophenyl)-ethyl]-cyclopentylamino}-1H-pyrazolo[3,4-d]pyrimidine
4-[N-(3-bromopyridin-5-yl-methyl)-cyclopentylamino]-1H-pyrazolo[3,4-d]pyrimidine
4-[N-(3-ethoxycarbonylbenzyl)-cyclopentylamino]-1-(2,3-dihydroxypropyl)-1H-pyrazolo[3,4-d]pyrimidine
4-[N-(3-aminocarbonylbenzyl)-cyclopentylamino]-1-(2,3-dihydroxypropyl)-1H-pyrazolo[3,4-d]pyrimidine
4-[N-(3-cyanobenzyl)-cyclopentylamino]-1-(2,3-dihydroxypropyl)-1H-pyrazolo[3,4-d]pyrimidine
4-[N-(2,5-dichlorobenzyl)-cyclopentylamino]-1-(2,3-dihydroxypropyl)-1H-pyrazolo[3,4-d]pyrimidine
4-[N-(3,4-dichlorobenzyl)-cyclopentylamino]-1-(2,3-dihydroxypropyl)-1H-pyrazolo[3,4-d]pyrimidine
4-[N-(5-chloro-2-methylbenzyl)-cyclopentylamino]-1-(2,3-dihydroxypropyl)-1H-pyrazolo[3,4-d]pyrimidine
4-[N-(2-chloro-5-methoxybenzyl)-cyclopentylamino]-1-(2,3-dihydroxypropyl)-1H-pyrazolo[3,4-d]pyrimidine The following Examples are given for the purpose of illustrating the present invention:

EXAMPLE 1

4-[N-(3-Chlorobenzyl)-cyclopentylamino]-1H-pyrazolo[3,4-d]pyrimidine

A mixture of 12.5 g. (80 mmole) 4-chloro-1H-pyrazolo[3,4-d]pyrimidine, 50.3 g. (240 mmole) N-(3-chlorobenzyl)-cyclopentylamino and 190 ml. n-butanol is heated to reflux for 16 hours and then evaporated. The residue is taken up in dilute aqueous sodium hydroxide solution, washed with diethyl ether, the aqueous phase neutralised with hydrochloric acid and the precipitate filtered off. After recrystallisation from ethanol, there are obtained 19.5 g. of the title compound (74% of theory); m.p. 186°–187° C.

EXAMPLE 2

In a manner analogous to that described in Example 1, by the reaction of 4-chloro-1H-pyrazolo[3,4-d]pyrimidine with the appropriate secondary amines, there are obtained the following compounds:

| | designation | yield % | melting point °C. (solvent) |
|---|---|---|---|
| (a) | 4-(N—allylcyclohexylamino)-1H—pyrazolo[3,4-d]pyrimidine | 46 | 141–143 (ethanol/water) |
| (b) | 4-[N—(3-methylbenzyl)-cyclopentylamino]-1H—pyrazolo-[3,4-d]pyrimidine | 49 | 143–145 (ethanol) |
| (c) | 4-[N—(3-trifluoromethylbenzyl)-cyclopentylamino]-1H—pyrazolo[3,4-d]pyrimidine | 76 | 171–172 (ethanol) |
| (d) | 4-[N—(3-methoxybenzyl)-cyclopentylamino]-1H—pyrazolo[3,4-d]pyrimidine | 63 | 169–170 |
| (e) | 4-[N—(5-chloro-2-methoxybenzyl)-cyclopentylamino]-1H—pyrazolo[3,4-d]pyrimidine | 40 | 232–235 (dichloromethane/methanol) |
| (f) | 4-[N—(3-bromobenzyl)-cyclopentylamino]-1H—pyrazolo-[3,4-d]pyrimidine | 55 | 192–194 (ethyl acetate) |
| (g) | 4-[N—(3-ethoxycarbonylbenzyl)-cyclopentylamino]-1H—pyrazolo[3,4-d]pyrimidine | 28 | 135–137 (ethyl acetate) |
| (h) | 4-[N—3-aminocarbonylbenzyl)-cyclopentylamino]-1H—pyrazolo[3,4-d]pyrimidine | 25 | 150–160 amorphous (diethyl ether) |
| (i) | 4-[N—(3-cyanobenzyl)-cyclopentylamino]-1H—pyrazolo-[3,4-d]pyrimidine | 52 | 178–180 (diethyl ether) |
| (j) | 4-[N—(2,5-dichlorobenzyl)-cyclopentylamino]-1H—pyrazolo[3,4-d]pyrimidine | 32 | 233–235 (diethyl ether) |
| (k) | 4-[N—(3,4-dichlorobenzyl)-cyclopentylamino]-1H—pyrazolo[3,4-d]pyrimidine | 27 | 168–170 (ligroin) |
| (l) | 4-[N—(5-chloro-2-methylbenzyl)-cyclopentylamino]-1H—pyrazolo[3,4-d]pyrimidine | 33 | 203–205 (ligroin) |
| (m) | 4-[N—(2-chloro-5-methoxybenzyl)-cyclopentylamino]-1H—pyrazolo[3,4-d]pyrimidine | 35 | 213–215 (diethyl ether) |
| (n) | 4-[N—(2,5-dimethylbenzyl)-cyclopentylamino]-1H—pyrazolo[3,4-d]pyrimidine | 41 | 188–190 (ligroin) |
| (o) | 4-[N—(2-furylmethyl)-cyclopentylamino]-1H—pyrazolo-[3,4-d]pyrimidine | 35 | 125–127 (ethanol) |
| (p) | 4-[N—(thiophen-2-ylmethyl)-cyclopentylamino]-1H—pyrazolo[3,4-d]pyrimidine | 56 | 166–169 (ligroin) |
| (q) | 4-[N—(2-methylpyridin-6-yl-methyl)-cyclopentylamino]-1H—pyrazolo[3,4-d]pyrimidine | 79 | 182–184 (ethanol) |
| (r) | 4-[N—(3-bromobenzyl)-2- | 31 | 173–175 |

-continued

| designation | yield % | melting point °C. (solvent) |
|---|---|---|
| propyl)-amino]-1H—pyrazolo-[3,4-d]pyrimidine | | (diethyl ether) |
| (s) 4-[N—(3-bromobenzyl)-3-pentyl)-amino]-1H—pyrazolo-[3,4-d]pyrimidine | 27 | 147–148 (diethyl ether) |
| (t) 4-[N—(2-bromobenzyl)-cyclopentylamino]-1H—pyrazolo-[3,4-d]pyrimidine | 29 | 216–217 (diethyl ether) |
| (u) 4-[N—(3-bromobenzyl)-cyclohexylamino]-1H—pyrazolo-[3,4-d]pyrimidine | 24 | 149–150 (diethyl ether) |
| (v) 4-[N—(3-bromobenzyl)-methyl-amino]-1H—pyrazolo[3,4-d]-pyrimidine | 55 | 216–217 (methanol) |
| (w) 4-[N—allyl-(3-bromobenzyl)-amino]-1H—pyrazolo[3,4-d]-pyrimidine | 52 | 118–120 (ethyl acetate) |
| (x) 4-(N—benzylcyclopentylamino)-1H—pyrazolo[3,4-d]pyrimidine | 28 | 168–170 (diethyl ether) |
| (y) 4-[N—(4-bromobenzyl)-cyclopentylamino]-1H—pyrazolo-[3,4-d]pyrimidine | 26 | 112–114 (diethyl ether) |
| (z) 4-[N—(3-iodobenzyl)-cyclopentylamino]-1H—pyrazolo-[3,4-d]pyrimidine | 24 | 182–184 (diethyl ether) |
| (aa) 4-[N—(3-hydroxybenzyl)-cyclopentylamino]-1H—pyrazolo[3,4-d]pyrimidine | 43 | 213–215 (diethyl ether) |
| (ab) 4-[N—(3-methylthiobenzyl)-cyclopentylamino]-1H—pyrazolo[3,4-d]pyrimidine | 48 | 116–118 (diethyl ether) |
| (ac) 4-[N—(3-t-butylbenzyl)-cyclopentylamino]-1H—pyrazolo[3,4-d]pyrimidine hydrochloride | 37 | 223–225 (ethyl acetate) |
| (ad) 4-[N—(3,5-dibromobenzyl)-cyclopentylamino]-1H—pyrazolo[3,4-d]pyrimidine | 17 | 182–184 (diethyl ether) |
| (ae) 4-[N—(3-bromo-4-methylbenzyl)-cyclopentylamino]-1H—pyrazolo[3,4-d]pyrimidine | 19 | 200–202 (diethyl ether) |
| (af) 4-[N—(3-bromobenzyl)-anilino]-1H—pyrazolo-[3,4-d]pyrimidine | 40 | 194–196 (methanol) |
| (ag) 4-[N—(2-bromothiophen-5-yl)-methyl)-cyclopentylamino]-1H—pyrazolo[3,4-d]pyrimidine | 33 | 155–156 (ethyl acetate) |

EXAMPLE 3

4-[N-(3-Chlorobenzyl)-cyclopentylamino]-1-(2,3-dihydroxypropyl)-1H-pyrazolo[3,4-d]pyrimidine To a suspension of 1.5 g. (30 mmole) 50% sodium hydride in 50 ml. N,N-dimethylformamide are added dropwise 9.6 g. (30 mmole) 4-[N-(3-chlorobenzyl)-cyclopentylamino]-1H-pyrazolo[3,4-d]pyrimidine (compound of Example 1) in 25 ml. N,N-dimethylformamide. The reaction mixture is stirred for 1 hour at 80° C., 10.0 g. (35 mmole) 4-(4-toluenesulphonyloxymethyl)-2,2-dimethyl-1,3-dioxolan in 25 ml. N,N-dimethylformamide are added thereto, the reaction mixture is further stirred for 3 hours at 80° C. and evaporated in a vacuum. The residue is taken up in water, extracted with dichloromethane and the extract evaporated. The residue is mixed with 300 ml. 0.1N hydrochloric acid, heated under reflux for 10 hours, allowed to cool, washed with diethyl ether and the aqueous phase rendered alkaline with aqueous sodium hydroxide solution. After extraction with dichloromethane and evaporation of the extract, there are obtained 8.2 g. of crude product which is purified by chromatography on silica gel (elution agent: dichloromethane/methanol; 9:1 v/v). 4.1 g. (34% of theory) of the title compound are eluted which, after trituration with diethyl ether, melts at 98°–100° C.

EXAMPLE 4

In a manner analogous to that described in Example 3, by alkylation with 4-(4-toluenesulphonyloxymethyl)-2,2-dimethyl-1,3-dioxolan, there are obtained the following compounds:

| designation | yield % | melting point °C. (solvent) |
|---|---|---|
| (a) 4-(N—allylcyclohexylamino)-1-(2,3-dihydroxypropyl)-1H—pyrazolo[3,4-d]pyrimidine from the compound of Example 2a) | 38 | oil |
| (b) 4-[N—(3-trifluoromethyl-benzyl)-cyclopentylamino]-1-(2,3-dihydroxypropyl)-1H—pyrazolo[3,4-d]pyrimidine from the compound of Example 2c) | 33 | 122–123 (diethyl ether) |
| (c) 4-[N—(2,5-dimethylbenzyl)-cyclopentylamino]-1-(2,3-dihydroxypropyl)-1H—pyrazolo[3,4-d]pyrimidine from the compound of Example 2n) | 35 | 60–70 amorphous (dichloromethane/methanol) |
| (d) 4-[N—(2-furylmethyl)-cyclopentylamino]-1-(2,3-dihydroxypropyl)-1H—pyrazolo[3,4-d]pyrimidine from the compound of Example 2o) | 40 | oil |
| (e) 4-[N—(thiophen-2-ylmethyl)-cyclopentylamino]-1-(2,3-dihydroxypropyl)-1H—pyrazolo[3,4-d]pyrimidine from the compound of Example 2p) | 44 | oil |
| (f) 4-[N—(3-methoxybenzyl)-cyclopentylamino]-1-(2,3-dihydroxypropyl)-1H—pyrazolo[3,4-d]pyrimidine from the compound of Example 2d) | 41 | oil hydrochloride 175–176 (ethyl acetate) |
| (g) 4-[N—(3-methylbenzyl)-cyclopentylamino]-1-(2,3-dihydroxypropyl)-1H—pyrazolo[3,4-d]pyrimidine | 65 | 80–82 (diethyl ether) |
| (h) 4-[N—(3-bromobenzyl)-cyclopentylamino]-1-(2,3-dihydroxypropyl)-1H—pyrazolo[3,4-d]pyrimidine | 51 | 107–108 (diethyl ether) |
| (i) 4-[N—(5-chloro-2-methoxybenzyl)-cyclopentylamino]-1-(2,3-dihydroxypropyl)-1H—pyrazolo[3,4-d]pyrimidine | 58 | 132–134 (diethyl ether) |

EXAMPLE 5

4-[N-(2,5-Dimethylbenzyl)-cyclopentylamino]-1-(tetrahydrofuran-2-yl)-1H-pyrazolo[3,4-d]pyrimidine A mixture of 7.8 g. (35 mmole) 4-chloro-1-(tetrahydrofuran-2-yl)-1H-pyrazolo[3,4-d]pyrimidine, 20.3 g. (100 mmole) N-(2,5-dimethylbenzyl)-cyclopentylamine and 100 ml. n-butanol is heated under reflux for 16 hours. The reaction mixture is evaporated, the residue is taken up in water and extracted with dichloromethane and the extract is washed with dilute acetic acid and dilute aqueous sodium hydrogen carbonate solution, dried, evaporated and chromatographed on silica gel. 5.0 g. (37% of theory) of the title compound are eluted with dichloromethane/methanol (98:2 v/v) which, after trituration with diethyl ether, melts at 173°–174° C.

EXAMPLE 6

In a manner analogous to that described in Example 5, by reaction of 4-chloro-1-(tetrahydrofuran-2-yl)-1H-pyrazolo[3,4-d]pyrimidine with an appropriate amine, there are obtained the following compounds:

| designation | yield % | melting point °C. (solvent) |
|---|---|---|
| (a) 4-(N—allylcyclohexylamino)-1-(tetrahydrofuran-2-yl)-1H—pyrazolo[3,4-d]pyrimidine | 29 | oil |
| (b) 4-[N—(2-furylmethyl)-cyclopentylamino]-1-tetrahydrofuran-2-yl)-1H—pyrazolo-[3,4-d]pyrimidine | 33 | 85–87 (ligroin/diethyl ether) |
| (c) 4-[N—(thiophen-2-ylmethyl)-cyclopentylamino]-1-tetrahydrofuran-2-yl)-1H—pyrazolo[3,4-d]pyrimidine | 46 | 120–122 (diethyl ether) |
| (d) 4-[N—(3-bromobenzyl)-cyclopentylamino]-1-(tetrahydrofuran-2-yl)-1H—pyrazolo-[3,4-d]pyrimidine | 44 | 118–119 (ligroin) |

EXAMPLE 7

Test Results for Pharmaceutical Activity

Activity of the inventive compounds was shown by the following testing in vitro. The testing result show inhibition of antigen-induced constriction of passively sensitized guinea pig pulmonary parenchyma strips in vitro (organ bath). The method employed was as described herewith:

Pirbright-White guinea pigs were stunned by a blow to the neck and bled. The lungs were flushed largely free of blood in situ with Krebs' buffer, pH 7.4.

Then the lung was removed, cut into strips (approx. 20×4×4 mm) and the strips were passively sensitized for one hour at room temperature with a 1:50 dilution of a homologous anti-ovalbumin antiserum and then washed once with Krebs' buffer.

The antiserum had previously been produced as described by Davies et al., (Quantitative studies on anaphylaxis in guinea pigs passively sensitized with homologous antibody. Inter. Arch. Allergy 41, 648–654 (1971)) in guinea pigs of the same strain by repeated injection of ovalbumin (2×crystallized) with the addition of complete Freund's adjuvant (Until it was used, the antiserum was stored undiluted at −18° C.).

Then the lung strips were fixed singly with one end to the bottom of 10-milliliter organ baths, and with the upper end to isometric measuring devices for the recording of the constrictions of the lung strips through an amplifier on a plotter. The tenseron was adjusted to 1.2 g weight.

Then the baths were filled with Krebs' buffer and continually gassed at 37° C. with $O_2$ (95%) and $CO_2$ (5%).

After a 30-minute equilibration phase, histamine control spasms were produced in order to establish the reactivity of the lung specimens, washed, then the test substance was preincubated for 20 minutes at 37° C., and the the ovalbumin constriction was produced.

The inhibiting action of the compounds according to the invention was expressed as percentage reduction of the constriction amplitude of the "specimens with the test substance" in proportion to the "untreated control constrictions."

TABLE
Inhibition of the antigen-induced constriction on the passively sensitized strip of pulmonary parenchyma (guinea pig)

| Substance from Example No. | Inhibition (%) Superfusion Concentration 10/μM |
|---|---|
| 2n | 32 |
| 2o | 39 |
| 2p | 37 |
| 4b | 36 |
| 2d | 36 |
| 2g | 40 |
| 2i | 35 |
| 2j | 29 |
| 2k | 32 |
| 2l | 32 |

It will be understood that the specification and examples are illustrative but not limitative of the present invention and that other embodiments with the spirit and scope of the invention will suggest themselves to those skilled in the art.

What is claimed:

1. Pyrazolo (3,4-d)pyrimidines of the formula:

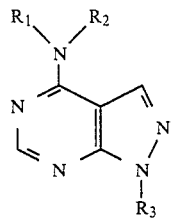

(I)

wherein $R_1$ is a $C_1$ to $C_6$-alkyl, a $C_2$ to $C_6$-alkenyl, a $C_3$ to $C_7$-cycloalkyl or a naphthyl or phenyl, $R_2$ is a $C_2$ to $C_6$-alkenyl, a $C_3$ to $C_7$-cycloalkyl or an unsubstituted or substituted phenyl-$C_1$–$C_6$-alkyl or hetero-$C_1$–$C_6$-alkyl wherein the hetero radical is a 5 or 6 membered ring selected from the group consisting of furyl, thienyl and pyridinyl and wherein said substituted phenyl-$C_1$–$C_6$-alkyl or hetero-$C_1$–$C_6$-alkyl is substituted from the group consisting of halogen, $C_1$ to $C_6$-alkyl, hydroxyl, $C_1$ to $C_6$-alkoxy, $C_1$ to $C_3$-haloalkyl, $C_3$ to $C_7$-alkoxycarbonyl, aminocarbonyl, $C_2$ to $C_7$-alkylaminocarbonyl, $C_3$ to $C_{13}$-dialkylaminocarbonyl, cyano and $C_1$ to $C_6$-alkylthio, and $R_3$ is hydrogen or is an unsubstituted $C_2$ to $C_6$-alkyl or is a substituted $C_2$–$C_6$ alkyl substituted at least once by hydroxyl or is a tetrahydrofuranyl or tetrahydropyranyl, with the proviso that $R_2$ cannot be an unsubstituted benzyl wherein $R_1$ is methyl and the physiologically acceptable salts thereof with inorganic and organic acids and the racemic or optically active forms thereof.

2. The compound of claim 1 wherein the alkyl is selected from the group consisting of methyl, ethyl, n-propyl, isopropyl, n-butyl, isobutyl, n-pentyl and 3-pentyl, the alkenyl is allyl, the alkoxy is methoxy or ethoxy and the alkylthio is methylthio or ethylthio.

3. The compound of claim 1 wherein the cycloalkyl is cyclopentyl or cyclohexyl, the heteroalkyl is furfuryl, thenyl or pyridinylmethyl, and the aralkyl is benzyl, phenethyl phenylpropyl, phenylisopropyl or 3-methyl-3-phenylisopropyl.

4. The compound of claim 1 wherein $R_2$ is benzyl is phenyl.

5. The compound of claim 1 wherein $R_3$ is selected from the group consisting of hydrogen, 2-hydroxyethyl, 2-hydroxypropyl, 2,3-dihydroxypropyl, tetrahydrofuran-2-yl and tetrahydropyran-2-yl.

6. A pyrazolo[3,4-d]pyrimidine compound designated 4-[N-(3-trifluoromethylbenzyl)-cyclopentylamino]-1-(2,3-dihydroxypropyl)-1H-pyrazolo[3,4-d]pyrimidine.

7. A pyrazolo[3,4-d]pyrimidine compound designated 4-[N-(3-methoxybenzyl)-cyclopentylamino]-1H-pyrazolo[3,4-d]pyrimidine.

8. A pyrazolo[3,4-d]pyrimidine compound designated 4-[N-(3-ethoxycarbonylbenzyl)-cyclopentylamino]-1H-pyrazolo[3,4-d]pyrimidine.

9. A pyrazolo[3,4-d]pyrimidine compound designated 4-[N-(3-cyanobenzyl)]cyclopentylamino]-1H-pyrazolo[3,4-d]pyrimidine.

10. A pyrazolo[3,4-d]pyrimidine compound designated 4-[N-(2,5-dichlorobenzyl)-cyclopentylamino]-1H-pyrazolo[3,4-d]pyrimidine.

11. A pyrazolo[3,4-d]pyrimidine compound designated 4-[N-(3,4-dichlorobenzyl)-cyclopentylamino]-1H-pyrazolo[3,4-d]pyrimidine.

12. A pyrazolo[3,4-d]pyrimidine compound designated 4-[N-(5-chloro-2-methylbenzyl)-cyclopentylamino]-1H-pyrazolo[3,4-d]pyrimidine.

13. A pyrazolo[3,4-d]pyrimidine compound designated 4-[N-(2,5-dimethylbenzyl)-cyclopentylamino-1H-pyrazolo[3,4-d]pyrimidine.

14. A pyrazolo[3,4-d]pyrimidine compound designated 4-[N-2-furylmethyl)-cyclopentylamino]-1H-pyrazolo-[3,4-d]pyrimidine.

15. A pyrazolo[3,4-d]pyrimidine compound designated 4-[N-(thiophen-2-ylmethyl)-cyclopentylamino]-1H-pyrazolo[3,4-d]pyrimidine.

16. A pharmaceutical composition for treating histamine-medicated allergic disease comprising an effective amount of the compound of claim 1 in a pharmaceutically acceptable carrier.

17. A pharmaceutical composition for treating histamine-medicated allergic disease comprising an effective amount on a compound in a pharmaceutically acceptable carrier wherein the compound is selected from at least one of the group consisting of 4-[N-(3-trifluoromethyl-benzyl)-cyclopentylamino]-1-(2,3-dihydroxypropyl)-1H-pyrazolo[3,4-d]pyrimidine, 4-[N-(3-methoxybenzyl)-cyclopentylamino]-1H-pyrazolo[3,4-d]pyrimidine, 4-[N-(3-ethoxycarbonyl-benzyl)-cyclopentylamino]-1H-pyrazolo[3,4-d]pyrimidine, 4-[N-(3-cyanobenzyl)-cyclopentylamino]-1H-pyrazolo[3,4-d]pyrimidine, 4-[N-(2,5-dichlorobenzyl)-cyclopentylamino]-1H-pyrazolo[3,4-d]pyrimidine, 4-[N-(3,4-dichlorobenzyl)-cyclopentylamino]-1H-pyrazolo[3,4-d]pyrimidine, 4-[N-(5-chloro-2-methylbenzyl)-cyclopentylamino]-1H-pyrazolo[3,4-d]pyrimidine, 4-[N-2,5-dimethylbenzyl)-cyclopentylamino]-1H-pyrazolo[3,4-d]pyrimidine, 4-[N-(2-furylmethyl)-cyclopentylamino]-1H-pyrazolo[3,4-d]pyrimidine and 4-[N-(thiophen-2-ylmethyl)-cyclopentylamino]-1H-pyrazolo[3,4-d]pyrimidine.

18. A method for treating histamine-medicated allergic disease in a patient having an allergic disease comprising administering an effective amount of a compound of claim 1 in a pharmacologically acceptable carrier.

19. A method for treating histamine-medicated allergic disease in a patient having an allergic disease comprising administering an effective amount in a pharmacologically acceptable carrier of at least one compound selected from the group consisting of 4-[N-(3-trifluoromethyl-benzyl)-cyclopentylamino]-1-(2,3-dihydroxypropyl)-1H-pyrazolo[3,4-d]pyrimidine, 4-[N-(3-methoxybenzyl)-cyclopentylamino]-1H-pyrazolo[3,4-d]pyrimidine, 4-[N-(3-ethoxycarbonyl-benzyl)-cyclopentylamino]-1H-pyrazolo[3,4-d]pyrimidine, 4-[N-(3-cyanobenzyl)-cyclopentylamino]-1H-pyrazolo[3,4-d]pyrimidine, 4-[N-(2,5-dichlorobenzyl)-cyclopentylamino]-1H-pyrazolo[3,4-d]pyrimidine, 4-[N-(3,4-dichlorobenzyl)-cyclopentylamino]-1H-pyrazolo[3,4-d]pyrimidine, 4-[N-(5-chloro-2-methylbenzyl)-cyclopentylamino]-1H-pyrazolo[3,4-d]pyrimidine, 4-[N-2,5-dimethylbenzyl)-cyclopentylamino]-1H-pyrazolo[3,4-d]pyrimidine, 4-[N-(2-furylmethyl)-cyclopentylamino]-1H-pyrazolo[3,4-d]pyrimidine and 4-[N-(thiophen-2-ylmethyl)-cyclopentylamino]-1H-pyrazolo[3,4-d]pyrimidine.

20. The method of claim 18 wherein 0.1 to 50 mg/kg body weight is administered daily.

21. The method of claim 19 wherein 0.1 to 50 mg/kg body weight is administered daily.

* * * * *